United States Patent [19]
Rodgers et al.

[11] Patent Number: 6,071,944
[45] Date of Patent: Jun. 6, 2000

[54] METHOD OF TREATMENT OF PIGMENTED CANCER CELLS UTILIZING PHOTODYNAMIC THERAPY

[75] Inventors: Michael A. J. Rodgers, Waterville, Ohio; Giulio Jori, Padova, Italy; Malcolm E. Kenney, Cleveland Heights, Ohio

[73] Assignee: Bowling Green State University, Bowling Green, Ohio

[21] Appl. No.: 08/999,866

[22] Filed: Nov. 12, 1997

[51] Int. Cl.$^7$ ...................................................... A01N 43/36
[52] U.S. Cl. ........................... 514/408; 514/63; 514/185; 514/410
[58] Field of Search .............................. 514/63, 408, 410, 514/185

[56] References Cited

PUBLICATIONS

Sarna et al., "Photosensitizaiton of Melanins: A comparative Study", Photochemistry and Photobiology vol. 42, No. 5, pp. 529–532, 1985.
Database CAPLUS on STN, No. 1996:168613, Young et al., "Photodynamic therapy of pigmented choroidal melanomas using a liposomal preparation of benzoporphyrin derivative." Arch. Opthalmol. (Chicago). Abstract, 1996 114(2), pp. 186–192.
Database BIOSIS on STN, No. 1993:255603, Gonzales et al., "Photodynamic Therapy of Pigmented Choroidal Melanomas" Investigtive Opthalmology & Visual Science. Abstract, 1995, 36(5), pp. 871–878.
Dougherty, T.J. (1987) Photosensitizers: therapy and detection of malignant tumours. Photochem. Photobiol., 45, 879–889.
Boyle R. W. and D. David (1996) Structure and biodistribution relationships of photodynamic sensitizers. Photochem. Photobiol. 64, 469–485.
Marcus S. (1996) Clinical photodynamic therapy; the continuing evolution. In Photodynamic therapy: basic principles and clinical application. Marcel Dekker New York (Edited by Henderson B. W. and Dougherty T. J.) pp 219–268.
Biolo. R., G. Jori, M. Soncin, R. Pratesi, U. Vanni, B. Rihter, M.E. Kenney and M. A. J. Rodgers (1994) Photodynamic therapy of B16 pigmented melanoma with liposome–delivered Si(IV)–naphathalocyanine. Photochem. Photobiol. 59, 362–365.
Biolo. R., G. Jori, M. Soncin, B. Rihter, M.E. Kenney and M. A. J. Rodgers (1996) Effect of photosensitizer delivery system and irradiation parameters on the efficiency of photodynamic therapy of B16 pigmented melanoma in mice. Photochem. Photobiol. 63, 224–228.
Sounik J. R., L. A. Schechtman, B. D. Rihther, W. E. Ford, M.A.J. Rodgers and M. E. Kenney (1990) Synthesis and characterization of naphthalocyanines and phthalocyanines of use in sensitizer studies. In Photodynamic Therapy: Mechanisms II, SPIE vol. 1203 (Edited by T. J. Dougherty and A.Katzir), pp. 224–232.

Anderson R. R. and J.A. Parrish (1982) Optical properties of human skin. In The science of photomedicine. Plenum Press, New York (Edited by Regan, J. D. and J.A. Parrish), pp. 174–194.
Anderson R. R., M. D. Margolis, S. Watenabe, T. Flotta, G. J. Hruza and J.S. Dover. (1989) Selective photothermolysis of cutaneous pigmentation by Q–switched Nd:YAG laser pulses at 1064, 532 and 355 nm. J. Invest. Dermatol., 93 28–32.
Anderson R. R. and J.A. Parrish (1983) Selective photothermolysis: precise microsurgery by selective absorption of pulses radiation. Science, 220 524–527.
Cuomo V., G. Jori, B. Rihter, M.E. Kenney and M. A. J. Rodgers (1990) Liposomes–delivered SI(IV)–naphthalocyanine as a photodynamic for experimental tumors: pharmacoikinetic and phototherapeutic studies. Br. J. Cancer 62, 966–970.
Fitzpatrick T. B., G Szabo (1959) The melanocyte : cytology and cytochemistry. J Invest Dermatol 32, 197–209.
Schuitmaker J. J., J.A van Best, J. L. van Delft, J. E. Jannink, J, A. Oosterhuis, G. F. J. M. Vrensen, D. de Wolff–Rouendaal, T. M. A. R. Dubbelman (1995) Photodynamic therapy of Hamster green melanoma in vitro using bacteriochlorin a as photosensitizer. In Photochemoterapy: Photodynamic Therapy and other modalities. SPIE vol. 2625 (Edited by Ehrenberg B., Jori G., Moan J.) pp 251–260.
Moan J., Q. Peng, V. Iani, L. Ma, R W. Horobin, K. Berg. M. Kongshang and J. M.Nesland (1995) Biodistribution, pharmacokinetic and in vivo fluorescence spectroscopic studies of photosensitizer. In Photochemotherapy: Photodynamic Therapy and other modalities. SPIE vol. 2625 (Edited by Ehrenberg B., Jori G., Moan J.) pp 234–250.
Schoenfeld N., R. Mamet, Y. Nordenberg, M. Shafran, T. Babushkin and Z. Malik. (1994). Phtoporphyrin biosynthesis in melanoma B16 cells stimulated by 5–aminolevulinic acid and chemical inducers: characterization of photodynamic inactivation. Inc. J. Cancer, 56 106–116.
Sarna T., I. A. Menon and R. C. Sealy (1985) Photosensitization of melains: a comparative study Photochem. Photobiol. 42 529–532.
Moan J., Peng Q., Iani V., Ma L., Horobin R., Berg K. and Kongshaug M. (1996) Bidistribution, pharmocokinetic and in vivo Flourescence spectroscopic studies of photosensitizers. SPIE 2625 234–250.

*Primary Examiner*—Dwayne C. Jones
*Attorney, Agent, or Firm*—Standley & Gilcrest LLP

[57] ABSTRACT

The present invention in general terms includes a method of treating cancerous cells containing a pigment, the method including irradiation of the cells with light of comprising the steps: (1) subjecting the cancerous cells to relatively high power light so as to substantially reduce the amount of the pigment in the cells; (2) treating the cancerous cells with one or more photosensitizing agent; followed by (3) subjecting the cancerous cells to relatively low power light so as to activate the photosensitizing agent(s).

7 Claims, 3 Drawing Sheets

METHOD OF TREATMENT OF PIGMENTED CANCER CELLS UTILIZING PHOTODYNAMIC THERAPY

STATEMENT OF GOVERNMENT INTEREST

This invention was made with government support under National Institute of Health Grant No. CA46281 awarded by the National Institute of Health. The Government of the United States of America may have certain rights in this invention.

TECHNICAL FIELD

The present invention is in the field of photodynamic therapy such as may be applied in treating cancers.

BACKGROUND

Photodynamic therapy (PDT) is a treatment that is based upon the differential uptake by cancerous cells of photosensitizing agents, followed by irradiation of the cells to cause a photochemical reaction that is believed to generate chemically disruptive species, such as singlet oxygen. These disruptive species in turn injure the cells through reaction with cell parts, such as cellular and nuclear membranes. Photodynamic therapy has been used successfully for treating several types of cancer cells.

However, certain types of cancers, such as the very virulent pigmented melanoma, are known to be poorly responsive to photodynamic therapy (PDT) with FDA-approved photosensitizing agents such as Photofrin, a haematoporphyrin derivative (1), as well as with several second generation phototherapeutic agents (2) whose lowest energy absorption band lies in the 600–700 nm spectral range. This lack of response is generally ascribed to optical filtering of the incident light by the melanin granules, which are expressed with a particularly high frequency in this tumor type.

One avenue taken used to address this problem has been to attempt to develop and use new photosensitizing agents that have energy absorption bands deeper in the infrared region than those mentioned above. One of the difficulties in this approach has been that such new photosensitizing agents are not as effective in their generation of disruptive species once irradiated, and they require further FDA approval.

Accordingly, it is an object of the present invention to develop effective techniques whereby pigmented cancer cells may be treated by PDT, including through techniques that apply efficient and approved photosensitizing agents.

In view of the present disclosure and the practice of the present invention, other advantages of the present invention may become apparent.

SUMMARY OF THE INVENTION

The present invention in general terms includes a method of treating cancerous tissues characterized by high concentrations of pigmented compounds, the method including irradiation of the neoplastic tissue with light of comprising the steps: (1) subjecting the cancer tissue to relatively high power light which is absorbed by the pigment so as to substantially reduce its amount in the pigmented cancerous cells; (2) treating the tumour with one or more photosensitizing agents;

followed by (3) subjecting the tumour tissue to relatively low power light absorbed by the photosensitizer so that the photosensitizer is promoted to a more reactive state and induces a series of chemical and biological events causing the disruption of the integrity of the tumour cells or their ability to maintain metabolism or reproduce.

As used herein, reference to substantial reduction of the amount of the pigment in the cells shall be understood as meaning reducing the amount of pigment in the cell so as to render it sufficiently translucent to the relatively low power light used to activate the photosensitizing agent(s).

The method of the present invention may be applied to any pigmented cancer cells, such as melanoma cells pigmented with melanin.

The relatively high power light may be provided by any appropriate light source such as by a laser adapted to provide high peak power laser irradiation. Typically, such high peak power laser irradiation preferably will provide submicrosecond pulsed power output of at least about $10^2$ mJ pulsed over 10 nanoseconds.

The one or more photosensitizing agent may be any photosensitizing agent, including those selected from the group consisting of tetrapyrrol-based photosensitizers, such as porphyrins (e.g., haematoporphyrin), chlorins, phthalocyanines and naphthalocyanines (e.g., such as Si(IV)-naphthalocyanine). Such photosensitizing agents may also include those selected from the group consisting of coumarins and psoralens.

DETAILED DESCRIPTION OF THE PREFERRED EMBODIMENTS

Figure 1A:
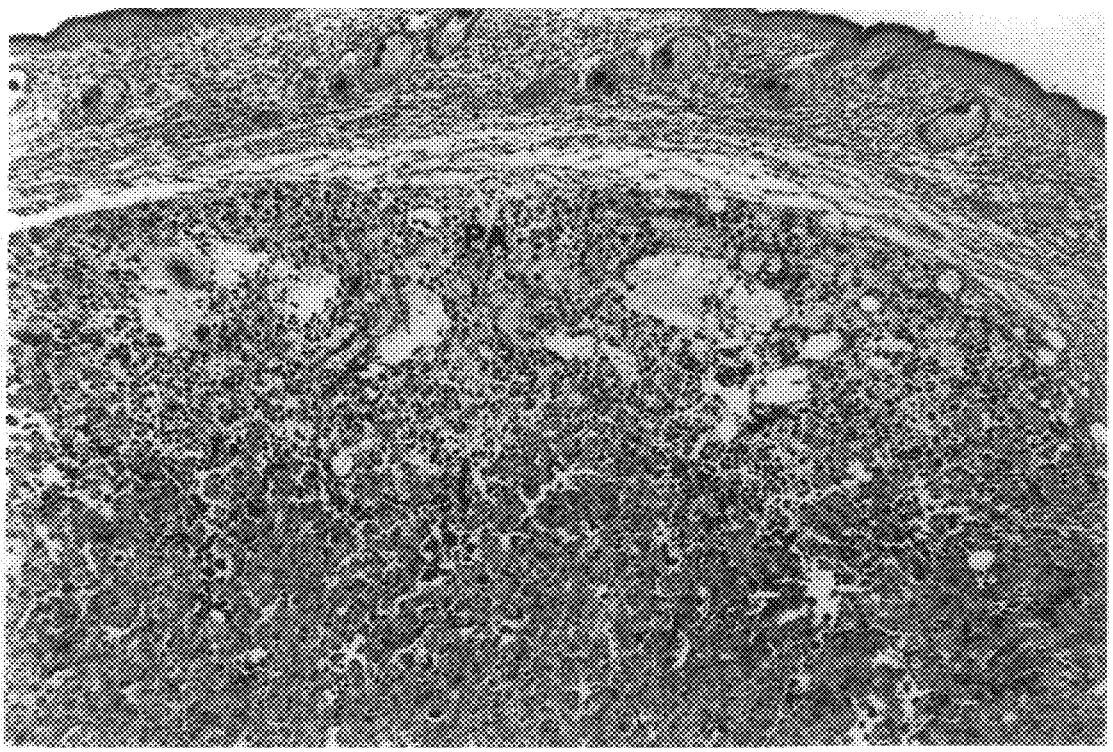
FIGS. 1A and 1B contain photographic histological images of a neoplastic mass and overlying skin taken immediately after irradiation in accordance with one embodiment of the present invention.

In accordance with the foregoing summary of the invention, the following describes preferred embodiments of the present invention which are presently considered to be the best mode of the invention.

Amelanotic melanoma has been shown to be successfully treated by Photofrin-PDT. Even a highly pigmented variety of melanoma, such as the B16 malignant melanoma, can be made to be responsive to PDT by using a naphthalocyanine photosensitizer, which is characterized by a large molar extinction coefficient (ca $5 \times 10^5$ M$^{-1}$ cm$^{-1}$) in the 770–790 nm wavelength interval. This tumor-loading naphthalocyanine can favorably compete for light absorption with melanin, whose absorbance decreases monotonically with increasing wavelength.

Although irradiation protocols on B16 melanoma-bearing mice administered with naphthalocyanine causes a marked delay in tumor regrowth after PDT in comparison with untreated control animals, no complete eradication of the melanoma was achieved probably because of insufficient light penetration to the deepest regions (4–5 mm) of this tumor model.

Accordingly, in order to further exploit the potential of phototherapeutic modalities for the treatment of highly pigmented tumors, the preferred embodiment of the present invention involves the association of conventional PDT with high peak power (HPP) laser irradiation adapted to eliminate pigment, such as in the particular case of melanin, with a Q-switched Nd:YAG laser delivering pulses of 1064 nm light. This wavelength is absorbed by melanin and can induce the selective photothermolysis of melanosomes, provided the Nd: YAG laser is operated in a submicrosecond pulsed regime so that the photoexcitation of the endogenous chromophore occurs in a time scale that is shorter than the thermal relaxation lime in the irradiated tissue.

In this way, the resulting temperature increase is spatially confined in the microenvironment of the melanin and the resulting fragmentation of melanosomes takes place without any detectable damage of the surrounding tissue compartments.

Using the method of the present invention, HPP laser treatment of subcutaneously implanted B16 pigmented melanoma allows a remarkable improvement in the response of the tumor to PDT with a naphthalocyanine photosensitizer.

Irradiation of B16 pigmented melanoma subcutaneously transplanted in C57 mice with a single 650 mJ pulse (10 ns) of 1064 nm light from a Q-switched Nd:YAG laser causes instantaneous bleaching of the pigmented tissue. Visual and histological examination of the resulting grey-colored tumor revealed the breakdown of melanosomes with no detectable alteration of the normal and tumor-overlying skin. Histological examination of the irradiated tumor shows some degree of vascular damage; the depth of the photodamage is not affected by the successive delivery of three consecutive light pulses. The bleached tumor grows at a modestly slower rate but the high peak power laser treatment does not affect the extent and time-dependency of tumor uptake for an intravenously injected photodynamic sensitizer Si(IV)-naphthalocyanine (isoBO—SiNc). Therefore, treatment of the B16 pigmented melanoma by photodynamic therapy (1 mg/kg isoBO—SiNc, 300 mW/cm$^2$–520 J/cm$^2$) from a 776 nm diode laser immediately after the 1064 nm irradiation results in a 11 days delay of tumor regrowth. This is markedly longer than the delay (4 days) obtained after photodynamic therapy under identical conditions without the pre-irradiation. Thus, pretreatment of pigmented tumors with high peak power light (such as 1064 nm light) appears to enhance their susceptibility to conventional photodynamic therapy.

The following is a detailed description of the materials and methods used in the preferred embodiment of the present invention.

Laser Sources

The laser source used in this example may be any laser having sufficient power out put to supply the light energy required.

Chemicals Bis(di-isobutyloctadecylsiloxy)-2,3-naphthalocyanato silicon (isoBO—SiNc) was prepared by chemical synthesis (6); its molar extinction coefficient in THF solution was found to be 5.6×105 M-1 cm-1 at 774 nm. DL—dipalmitoyl-phosphatidylcholine (DPPC) was obtained from Sigma Chemical Co. as a>98% pure crystalline product and used as received. The incorporation of isoBO—SiNc into unilamellar liposomes of DPPC was performed by a sonication procedure as detailed elsewhere (10). All other chemicals and solvents were commercial products of at least analytical reagent grade.

Animals and Tumors

Female C57/BL6 and BALB/C mice (18–20 g body weight) obtained from Harlan Spraque Dawley, Inc. (Indianapolis, Ind.) were used as experimental models. B16 pigmented melanoma (the B16 cell line was obtained from American Type Culture Collection) was subcutaneously transplanted into the upper flank by injecting 201(106 cells) of a sterile cell suspension in PBS. The cell line was cultured in Dulbecco's modified minimal essential medium supplemented with 10% fetal calf serum. The cell culture was maintained at 37° C. in a humidified atmosphere of 5% $CO_2$ in air. All of our experiments were performed at 5–7 days after injection of B16 melanoma cells, when the tumor volume was in the range of 0.02–0.04 cm$^3$ with an external diameter of 0.4–0.6 cm and a depth of 0.15–0.2 cm.

Pharmacokinetic Studies

SiNc incorporated into DPPC liposomes was injected at a dose of 1 mg/kg body weight into the caudal vein of C57 mice bearing the B16 pigmented melanoma. Three groups of mice (three mice per each time point) were used: (a) unirradiated control mice; (b) mice injected immediately after irradiation with the Nd: YAG laser (1064 nm, one pulse, 650 mJ); (c) mice injected at 24 h or 48 h before irradiation under the same conditions indicated for group (b). In all cases, at 3, 24 and 48 h after injection of isoBO—SiNc (groups a and b) and immediately after irradiation (group c), the mice were sacrificed by prolonged exposure to ether vapor. The blood was rapidly taken, centrifuged at 3000 rpm for 10 min. to remove the erythrocytes, and the serum was analyzed for its isoBO—SiNc content by a spectrophotofluorimetric procedure (4) using 690 nm as the excitation wavelength. The liver, tumor and peritumoral skin (namely an area with a 0.5 cm width surrounding the tumor) were excised and their isoBO—SiNc content was determined spectrophotofluorimetrically as previously described (4,5).

High Peak Power Irradiation of Healthy Mouse Skin and B16 Pigmented Melanoma

The dorsal and abdominal areas of C57 and BALB/c mice were shaved at 2 days before exposure to light. Animals were anesthetized with i.p. injected Ketamine. Different single pulse energies (100, 200, 300, 500 mJ) were delivered at 532 nm and at 1064 nm and the gross response of the cutaneous tissue was observed immediately and for a period of 24 h after irradiation. In a different set of experiments, C57 mice bearing the B16 pigmented melanoma were exposed to a succession of consecutive pulses of 1064 nm light (300, 500, 650 mJ per pulse) from the Nd: YAG laser. The phototreated mice were visually observed; and tumor specimens (one mouse per each irradiation experiment) were taken immediately and at 24 h after irradiation for light microscopic observation. In order to visualize the melanocytes the tumors were fixed in Dietrich's solution, dehydrated, embedded in paraffin and routinely sectioned. Sections were stained with hematoxylin-eosin and Fontana Masson silver stain (11).

Photodynamic Therapy and High Peak Power Irradiation Studies

When the tumor diameter was in the range of 0.4–0.6 cm, groups of 7–8 B16 melanoma bearing mice were irradiated with 1064 nm light from the Nd: YAG laser at 500 or 650 mJ per pulse (HPP). In one group of mice at 24 h after isoBO—SiNc injection (1 mg/kg) the tumor area was exposed to 774 nm light from a dye laser which was operated at a fluence rate of 300 mW/cm$^2$ for a total light fluence of 520 J/cm$^2$. This PDT treatment was performed, in other two groups, also before or after the tumors had been exposed to 1064 nm light from the Nd: YAG (650 mJ). Another group of 8 mice was treated with PDT (isoBO—SiNc 1 mg/kg, 300 mW/cm$^2$, 520 J/cm$^2$) preceded by HPP (1064 nm, 650 mJ) and retreated in the same way 10 days later, when the tumors were regrowing.

In a parallel set of experiments, a sequential treatment involving HPP and PDT (with the same irradiation conditions mentioned above) was followed by an immediate further irradiation at 550 mW/cm$^2$ and 200 j/cm$^2$ from the same 774 nm light. For each group the effectiveness of the treatment was evaluated by comparing the rate of tumor growth of the irradiated mice with that observed for control mice transplanted simultaneously with the phototreated mice but not exposed to light and not injected with isoBO—SiNc. The tumor size was measured daily by means of a caliper. Individual tumor volumes (V) were calculated by assuming a hemiellipsoidal structure for the tumor nodule and measuring the two perpendicular axes (a and b) and the height (c). Application of the relationship V 2/3(a/2×b/2×c) provided the tumor volume. The time to reach a defined tumor volume was calculated for the individual tumors.

Results
High Peak Power Irradiation of Normal Skin

C57 black mice and albino BALB/c mice are characterized by a lightly pigmented and a non-pigmented skin, respectively. For both animal strains, HPP Nd:YAG irradiation causes no detectable alteration of cutaneous tissue even under the most drastic irradiation conditions used by us. These observations are in agreement with previous findings which registered no damage of albino skin of Guinea pigs exposed to 1064 nm HPP light. The lack of cutaneous damage after 1064 nm HPP irradiation is further confirmed by histological analyses (see below). On the other hand, 532 nm HPP irradiation at both 300 mJ and 500 mJ induced the appearance of a purpuric macule in both types of mice. This is believed to reflect the onset of a limited microvascular damage caused by absorption of the incident light by hemoglobin (8).

High Peak Power Irradiation of Pigmented Melanoma

Figure 1B:
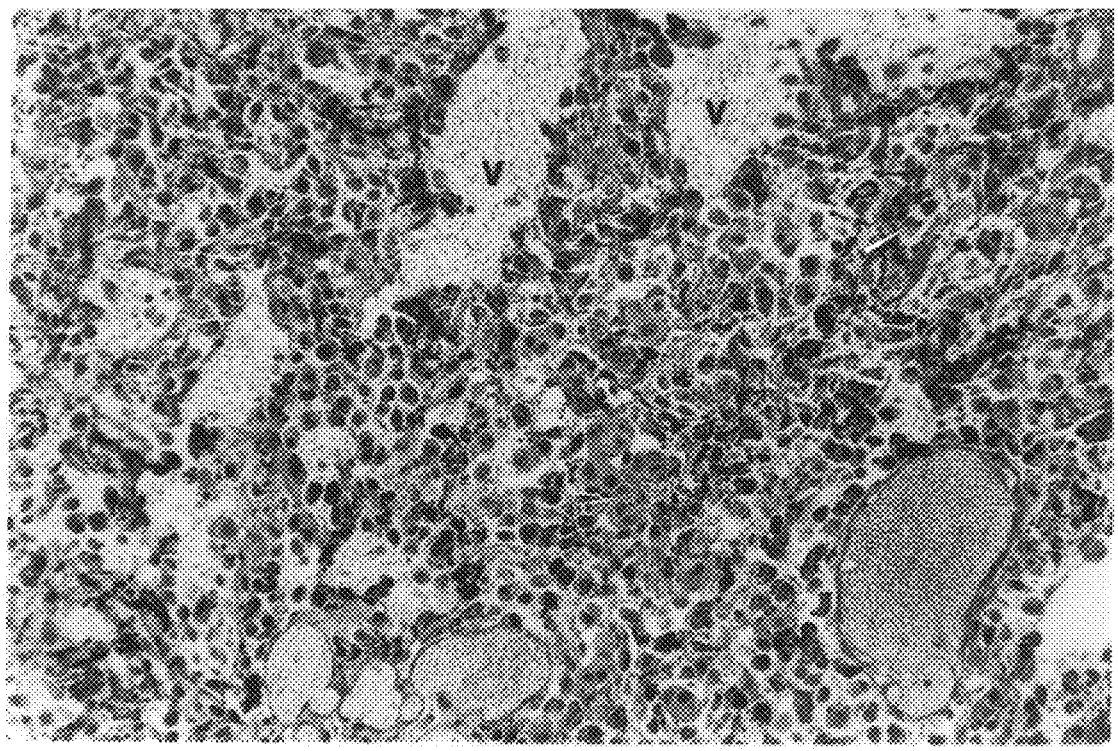

FIG. 1 shows a histological image of neoplastic mass and overlying skin taken immediately after irradiation of B16 pigmented melanoma with Nd:YAG at 1064 nm, 650 ml, one pulse, hematoxylin-cosin and Fontana Masson stain. Photograph A shows a large photodamaged area (PA) presenting pyknotic nuclei and some dilated blood vessels×53; and photograph B shows a magnified detail of damaged vessels which are rich of erythrocytes, without walls and often fused (V)×134.

Figure 2A:
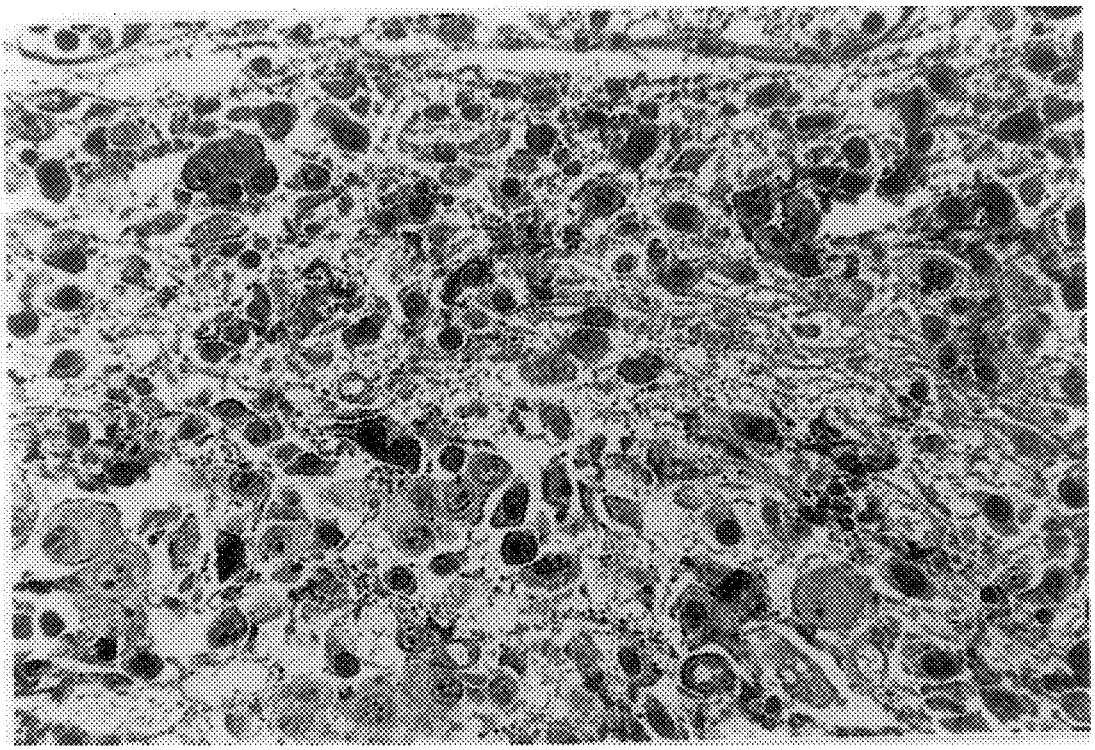
FIGS. 2A and 2B contain photographic histological images of a neoplastic mass and overlying skin taken immediately after irradiation in accordance with one embodiment of the present invention.
Figure 2B:
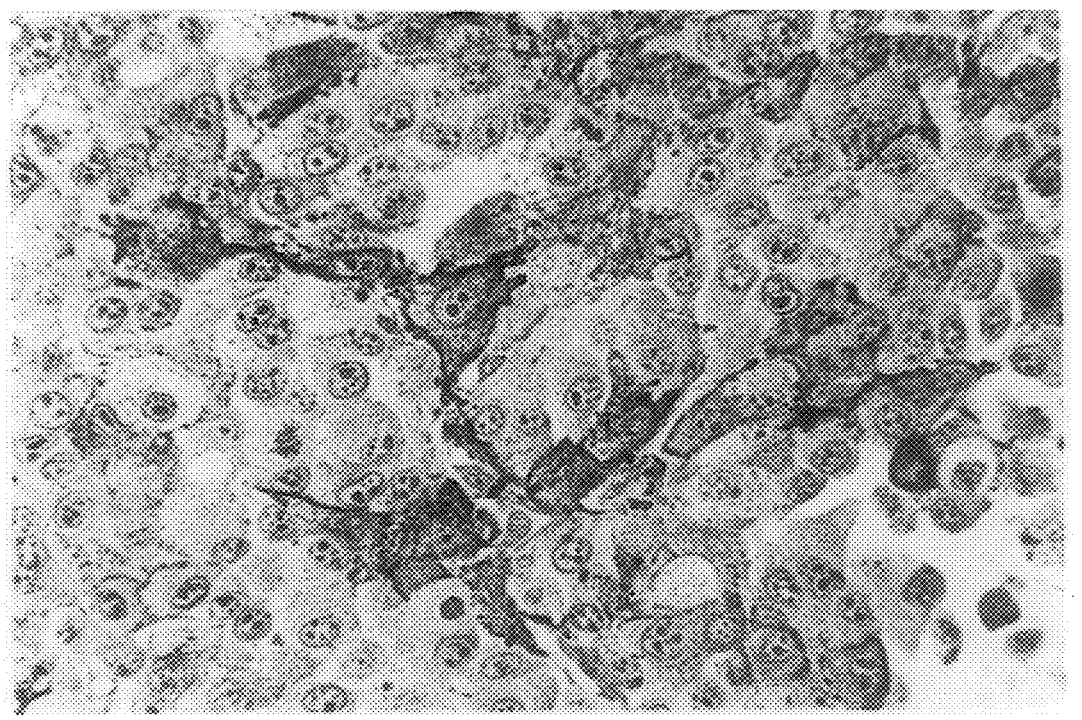

FIG. 2 shows magnified details of melanoma tumour taken immediately after irradiation with Nd:YAG at 1064 nm, 500 mJ, one pulse; hematoylin-cosin and Fontana Masson stain×335. Photograph A shows a photodamaged area characterized by a lack of the black staining which is produced by melanin pigment reduction of Ag$^+$ to Ag$^0$ (Fontana Masson solution). Photograph B shows an undamaged area presenting well preserved cells and the typical black staining formed by reaction between melanin and Ag.

Irradiation of the subcutaneously transplanted B16 pigmented melanoma in C57 mice with 1064 nm (300 mJ) HPP light caused no visible alteration of the light-exposed tissues. Exposure to 500 mJ or 650 mJ HPP pulses at 1064 nm resulted in the immediate formation of a white area with the dimension of the laser beam cross-section at the target. This bleached area faded in not less than 10 h. This observation suggests the occurrence of photoinduced modification of the tumor and/or overlying skin by the HPP 1064 nm light. A more precise description of the photoeffects was provided by histological studies. Thus, the structural features of the tumors and overlying skin obtained from control mice were essentially identical with those observed for tissue specimens isolated from mice exposed to 300 mJ pulses. On the other hand, a typical histological picture obtained from mice irradiated with 650 mJ pulses is shown in photograph A of FIG. 1. Clearly, while the cutaneous tissue is well preserved, the neoplastic mass exhibited an extensive alteration of cell morphology with pyknotic nuclei and significant vascular damage. The latter effect was more evident when the sections were observed under a greater magnification (see photograph B of FIG. 1).

Moreover, the damaged districts of the irradiated tumor were characterized (see photograph A of FIG. 2) by an almost complete disappearance of melanin pigments as compared to the undamaged areas (see photograph B of FIG. 2). The histological features of tumors treated with 500 mJ pulses were qualitatively similar with those treated with 650 mJ pulses, however the vascular damage was less extensive. These phototreated pigmented melanoma grew at a somewhat reduced rate in comparison with unirradiated melanoma (see graph shown in FIG. 3).

Figure 3:
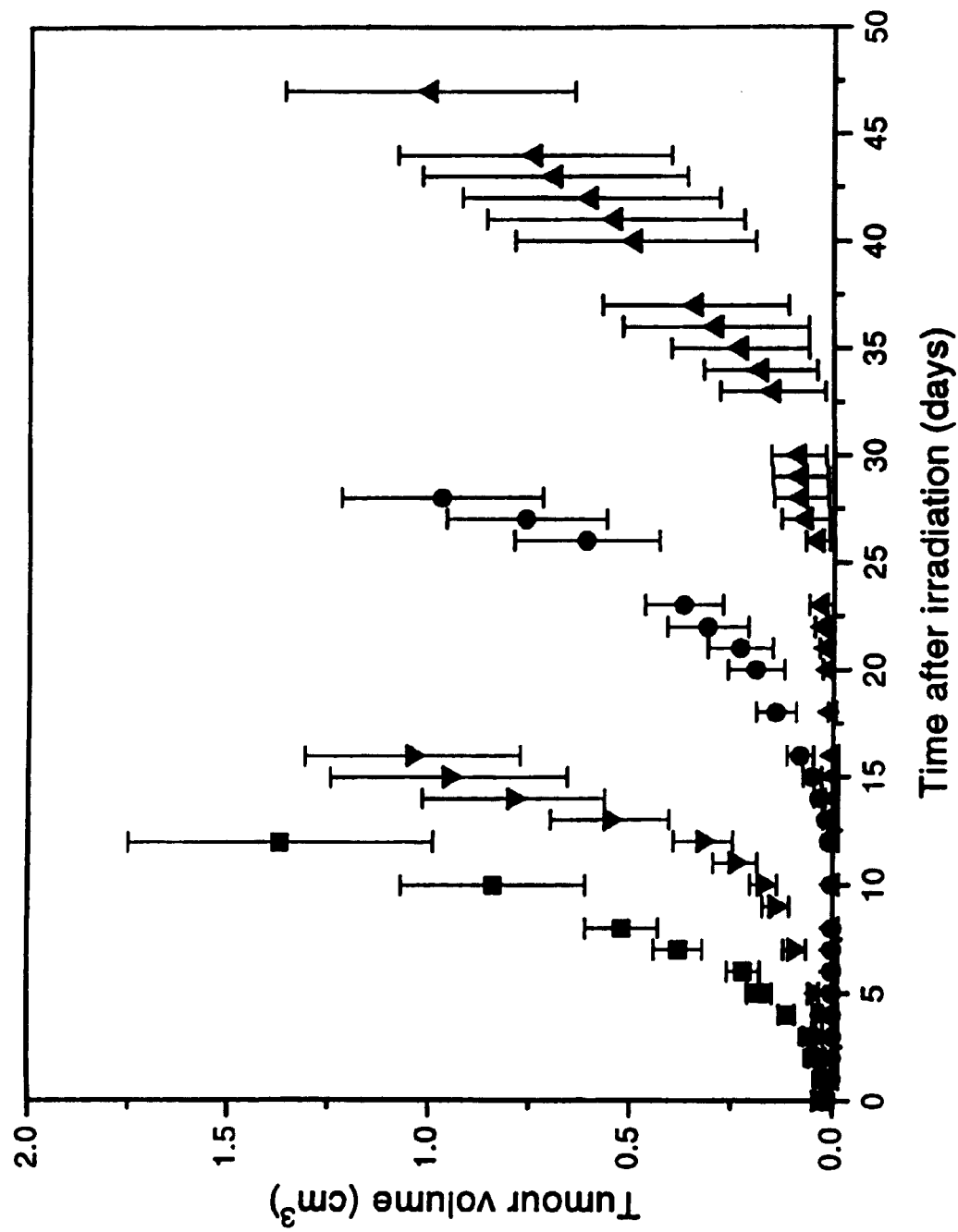
FIG. 3 is a graph showing a comparison of the rate of tumour growth in untreated and unirradiated mice, showing the comparative effects of a method in accordance with one embodiment of the present invention.

FIG. 3 shows a graph of the rate of tumour growth for mice injected with isoBO—SiNc (1 mg/kg) and after 24 h irradiated with: 300 mW/cm$^2$ and 520 J/cm$^2$ of 774 nm light followed by 650 mJ/pulse of 1064 nm (▼); 650 mJ/pulse of 1064 nm followed by 300 mW/cm$^2$ and 520 J/cm$^2$ of 774 nm light(●); 650 mJ/pulse of 1064 nm followed by 300 mW/cm$^2$ and 520 J/cm$^2$ of 774 nm light followed by 550 mW/cm$^2$ and 200 J/cm$^2$ of 774 nm light (▲); showing a comparison with the rate of tumour growth in untreated and unirradiated mice(■). Each point represents the average of seven±SE.

The delay was about two days in the case of tumors irradiated with 650 mJ pulses. Irradiation of the pigmented melanoma at 1064 nm with three consecutive pulses at 650 mJ induced a somewhat more extensive vascular damage, although the depth profile of the damage was unchanged. Moreover, the rate of post-irradiation tumor growth was identical with that observed after delivery of a single 650 mJ pulse (FIG. 3).

Combined Action of High Peak Power Irradiation and Photodynamic Therapy

The pharmacokinetic behavior of systematically injected isoBO—SiNc in unirradiated and 1064 nm-irradiated (650 mJ, one pulse) C57 mice is shown in Table 1.

TABLE 1

Recovery of isoBO-SiNc from selected tissues (μg of drug per g) and serum (μg/ml) of C57 mice bearing a B16 pigmented melanoma at various times after injection of 1 mg/kg photosensitizer.

| | 3h | | 24h | | | 48h | | |
|---|---|---|---|---|---|---|---|---|
| Sample | C | I | C | I | II | C | I | II |
| serum | 7.98 ± 0.7 | 8.92 ± 1.3 | 0.78 ± 0.2 | 0.8 ± 0.1 | 0.49 ± 0.1 | 0.29 ± 0.1 | 0.23 ± 0.0 | 0.12 ± 0.0 |
| liver | 8.87 ± 0.6 | 7.37 ± 0.5 | 10.6 ± 1.7 | 7.40 ± 0.5 | 9.25 ± 0.2 | 7.20 ± 0.4 | 8.63 ± 1.7 | 7.89 ± 0.5 |

TABLE 1-continued

Recovery of isoBO-SiNc from selected tissues (μg of drug per g) and serum (μg/ml) of C57 mice bearing a B16 pigmented melanoma at various times after injection of 1 mg/kg photosensitizer.

| Sample | 3h | | 24h | | | 48h | | |
|---|---|---|---|---|---|---|---|---|
| | C | I | C | I | II | C | I | II |
| tumour | 0.62 ± 0.1 | 0.70 ± 0.1 | 0.55 ± 0.1 | 0.52 ± 0.1 | 0.46 ± 0.1 | 0.42 ± 0.1 | 0.39 ± 0.1 | 0.35 ± 0.1 |
| peritumoural skin | 0.44 ± 0.1 | 0.44 ± 0.1 | 0.38 ± 0.1 | 0.39 ± 0.1 | 0.38 ± 0.1 | 0.38 ± 0.1 | 0.40 ± 0.1 | 0.41 ± 0.1 |

C = control mice (mice not irradiated)
I = mice injected immediately after irradiation (1064 nm, 650 mJ, I pulse)
II = mice injected at 24 and 48 h before irradiation (1064 nm, 650 mJ, 1 pulse)
Values ± SD; three mice were independently analyzed each time, with the exception of I where six mice were analyzed.

Special attention was paid to the recoveries obtained at 24 h and 48 h after injection since these time intervals correspond with the maximum isoBO—SiNc accumulation in a variety of transplanted tumors and are generally used for PDT. The data obtained for control mice were in good agreement with those previously found in our laboratory. Clearly, the biodistribution of isoBO—SiNc in the two groups of HPP-irradiated mice was essentially similar to that typical of unirradiated animals. Therefore, it appears that a prior HPP Nd:YAG irradiation of melanoma at 1064 nm has no influence on the accumulation and clearance of isoBO—SiNc from the tumor and other normal tissues (data from group I in Table 1). Moreover, our irradiation conditions have no appreciable effect on the recovery of isoBO—SiNc, which indicate that, as anticipated, the naphthalocyanine is not affected by 1064 nm light (data from group II in Table 1). On the basis of the above described findings, a PDT experiment (776 nm; 300 mW/cm$^2$–520 J/cm$^2$) was performed at 24 h post injection, immediately after HPP irradiation with a single 650 mJ pulse of 1064 nm light. The data are presented in FIG. 3, which shows that the animals were essentially tumor-free for some 11 days post-PDT, after which tumor re-growth occurred.

Table 2 presents data showing the effect of various irradiation protocols on tumor regrowth. The data indicate that tumor regrowth is substantially attenuated following an irradiation protocol in accordance with one embodiment of the present invention.

TABLE 2

Effect of different irradiation protocol on tumour regrowth

| Photosensitizer | Irradiation protocol | Mice tumour free time | Regrowth delay (days) |
|---|---|---|---|
| — | HPP | 0 | 3.7 |
| isoBO-SiNc | PDT | 2 | 6.3 |
| isoBO-SiNc | PDT + HPP | 2 | 7 |
| isoBO-SiNc | HPP + PDT | 9 | 16.4 |
| isoBO-SiNc | HPP + PDT + HPP + PDT | 21 | 27 |
| isoBO-SiNc | HPP + PDT + PTT | 22 | 34.6 |

HPP: High Peak Power irradiation from Nd: YAG laser, 1064 nm, 650 ml per pulse
PDT: Photodynamic Therapy from dye laser, 774 nm, 300 mW/cm$^2$, 520 J/cm$^2$
PTT: Photothermal Therapy from dye laser, 774 nm, 550 mW/cm$^2$, 200 J/cm$^2$
*Difference between the growth time for treated and control mice. The growth time is the time interval for the tumour to grow to a volume of 1 cm$^3$ from the size at the time of irradiation (0.03–0.04 cm$^3$). The growth time of control mice was 11 days.

Discussion

The major findings from the foregoing example are that (i) a single 10 ns pulse of 1064 nm light at 650 mJ per pulse causes immediate bleaching of the black pigmentation of malignant melanoma; (ii) this treatment causes no alteration in the pharmacokinetic profiles of isoBO—SiNc photosensitizer administered 24 h post to the HPP treatment; (iii) conventional PDT treatment using an 776 nm light immediately following HPP treatment induces a remarkable retardation in tumor growth rate as compared to both control mice and mice exposed only to HPP treatment (FIG. 3). Several experimental approaches have been explored in order to achieve an efficient phototherapeutic treatment of pigmented melanoma. The limited success of such approaches has been ascribed to the light-filtering action of the melanosomes, although a physical and/or chemical quenching of the photoprocesses by melanin cannot be completely ruled out.

The results described in the foregoing example clearly show that, whatever the mechanism of melanin photoprotection, this limiting factor can be overcome by pre-treating the highly pigmented tumor with 10 ns pulses of 1064 nm light at energies above 500 mJ per pulse. This causes a marked photobleaching of the melanin pigments while lightly pigmented tissues appear to be unaffected. This is in agreement with the findings of previous authors.

The histological analyses performed on specimens of Nd:YAG-irradiated B16 pigmented melanoma demonstrate an extensive rupture of melanosomes. However, a certain degree of vascular damage is also apparent; the morphological features of altered vessels (e.g. the dilated volume) are typical of thermally-injured tissues. The extent of photodamage, but not the depth profile, can be somewhat enhanced by increasing the number of consecutive pulses. The pre-treatment by HPP 1064 nm light alone induces a modest (2-days) growth delay as compared to unirradiated controls (FIG. 3). Although not limited to any theory of activity this partial effect is believed to be because the nanosecond pulse regime adopted here does not completely prevent some thermal diffusion to the exterior of the melanin microenvironment. The thermal relaxation time of melanin has been estimated to be in the picosecond range. The selectivity may perhaps be improved through a more precise choice of the operation conditions of the Nd:YAG laser.

It is particularly advantageous that the rate and extent of tumor accumulation of the photosensitizer isoBO—SiNc are not affected by the HPP Nd:YAG irradiation immediately prior to its intravenous injection. As a consequence, once a significant fraction of the melanosomes have been destroyed, a major obstacle to efficient PDT treatment has been removed. This observation encourages the hypothesis that the HPP pre-treatment may be useful for clearing the way for the employment of other photosensitizer families in melanoma therapy.

In summary, the experimental phototherapeutic investigations involving HPP irradiation followed by PDT with isoBO—SiNc delivered via DPPC liposomes demonstrate the occurrence of a significant tumor response which is markedly larger than that obtained with either treatment alone. Accordingly, the present invention provides a new way to phototherapeutic treatment of highly pigmented tumors.

REFERENCES

1 Dougherty, T. J. (1987) Photosensitizers: therapy and detection of malignant tumours. Photochem. Photobiol., 45, 879–889
2. Boyle R. W. and D. David (1996) Structure and biodistribution relationships of photodynamic sensitizers. Photochem. Photobiol. 64, 469–485.
3. Marcus S. (1996) Clinical photodynamic therapy: the continuing evolution. In Photodynamic therapy: basic principles and clinical application. Marcel Dekker New York (Edited by Henderson B. W. and Dougherty T. J.) pp 219–268.
4. Biolo. R., G. Jori, M. Soncin, R. Pratesi, U. Vanni, B. Rihter, M. E. Kenney and M. A. J. Rodgers (1994) Photodynamic therapy of B16 pigmented melanoma with liposome-delivered Si(IV)-naphathalocyanine. Photochem. Photobiol. 59, 362–365.
5. Biolo. R., G. Jori, M. Soncin, B. Rihter, M. E. Kenney and M. A. J. Rodgers (1 996) Effect of photosensitizer delivery system and irradiation parameters on the efficiency of photodynamic therapy of B16 pigmented melanoma in mice. Photochem. Photobiol. 63,224–228.
6. Sounik J. R., L. A. Schechtman, B. D. Rihther, W. E. Ford, M. A. J. Rodgers and M. E. Kenney (1990) Synthesis and characterization of naphthalocyanines and phthalocyanines of use in sensitizer studies. In Photodynamic Therapy: Mechanisms II. SPIE Vol. 1203 (Edited by T. J. Dougherty and A. Katzir), pp. 224–232.
7. Anderson R. R. and J. A. Parrish (1982) Optical properties of human skin. In The science of photomedicine. Plenum Press, New York (Edited by Regan, J. D. and J. A. Parrish), pp. 174–194.
8. Anderson R. R., M. D. Margolis, S. Watenabe, T. Flotta, G. J. Hruza and J. S. Dover. (1989) Selective photothermolysis of cutaneous pigmentation by Q-switched Nd:YAG laser pulses at 1064, 532 and 355 nm. J. Invest. Dermatol., 93 28–32.
9. Anderson R. R. and J. A. Parrish (1983) Selective photothermolysis: precise microsurgery by selective absorption of pulses radiation. Science, 220 524–527.
10. Cuomo V., G. Jori, B. Rihter, M. E. Kenney and M. A. J. Rodgers (1990) Liposomes-delivered Si(IV)-naphthalocyanine as a photodynamic for experimental tumors: pharmacokinetic and phototherapeutic studies. Br. J. Cancer 62, 966–970.
11. Fitzpatrick T. B., G Szabo (1959) The melanocyte:cytology and cytochemistry. J Invest Dermatol 32, 197–209.
12. Schuitmaker J. J., J. A van Best, J. L. van Delft, J. E. Jannink, J, A. Oosterhuis, G. F. J. M. Vrensen, D. de Wolff-Rouendaal, T. M. A. R. Dubbelman (1995) Photodynamic therapy of Hamster green melanoma in vitro and in vivo using bacteriochlorin a as photosensitizer. In Photochemoterapy: Photodynamic Therapy and other modalities. SPIE Vol 2625 (Edited by Ehrenberg B., Jori G., Moan J.) pp 251–260.
13. Moan J., Q. Peng, V. Iani, L. Ma, R. W. Horobin, K. Berg, M. Kongshang and J. M. Nesland (1995) Biodistribution, pharmacokinetic and in vivo fluorescence spectroscopic studies of photosensitizer. In Photochemotherapy: Photodynamic Therapy and other modalities. SPIE Vol 2625 (Edited by Ehrenberg B., Jori G., Moan J.) pp 234–250.
14. Schoenfeld N., R. Mamet, Y. Nordenberg, M. Shafran, T. Babushlkin and Z. Malik. (1994). Photoporphyrin biosynthesis in melanoma B16 cells stimulated by 5-aminolevulinic acid and chemical inducers: characterization of photodynamic inactivation. Inc. J. Cancer, 56 106–116.
15. Sarna T., I. A. Menon and R. C. Scaly (1985) Photosensitization of melanins: a comparative study Photochem. Photobiol. 42 529–532.

All of the foregoing references are incorporated herein by reference.

The preferred embodiments herein disclosed are not intended to be exhaustive or to unnecessarily limit the scope of the invention. The preferred embodiments were chosen and described in order to explain the principles of the present invention so that others skilled in the art may practice the invention. Having shown and described preferred embodiments of the present invention, it will be within the ability of one of ordinary skill in the art to make alterations or modifications to the present invention, such as through the substitution of equivalent materials or structural arrangements, so as to be able to practice the present invention without departing from its spirit as reflected in the appended claims. It is the intention, therefore, to limit the invention only as indicated by the scope of the claims.

What is claimed is:

1. A method of treating cancerous cells containing a pigment, said method comprising the steps:
    (1) subjecting said cancerous cells to relatively high power pulsed light so as to substantially reduce the amount of said pigment in said cells; followed by
    (2) treating said cancerous cells with at least one photosensitizing agent; followed by
    (3) subjecting said cancerous cells to relatively low power light so as to cause said at least one photosensitizing agent to undergo a photochemical reaction.

2. A method according to claim 1 wherein said cancerous tissue are pigmented melanoma cells.

3. A method according to claim 1 wherein said relatively high power light is provided by high peak power laser irradiation.

4. A method according to claim 3 wherein said relatively high power light is provided by submicrosecond pulsed high peak power laser irradiation.

5. A method according to claim 3 wherein said relatively high power light is provided by high peak power laser irradiation providing at least $10^2$ mJ pulsed over 10 nanoseconds.

6. A method according to claim 1 wherein said at least one photosensitizing agent is selected from the group consisting of tetrapyrrole-based photosensitizers, including porphyins, chlorins, phthalocyanines and napthalocyanines, as well from the group consisting of coumarins and psoralens.

7. A method according to claim 6 wherein said at least one photosensitizing agent is Si(IV)-naphthalocyanine.

* * * * *

UNITED STATES PATENT AND TRADEMARK OFFICE
CERTIFICATE OF CORRECTION

PATENT NO.   : 6,071,944
DATED        : June 6, 2000
INVENTOR(S)  : Rodgers et al.

It is certified that error appears in the above-identified patent and that said Letters Patent is hereby corrected as shown below:

In column 3, line 11, please delete the word "lime" and replace it with -- time --.

In column 5, line 47, please delete the word "hematoylin-cosin" and replace it with -- hematoylin-eosin --.

In column 10, line 9, please delete the word "Babushlkin" and replace it with -- Babushkin --.

In column 10, line 14, please delete the word "Scaly" and replace it with -- Sealy --.

Signed and Sealed this

Tenth Day of April, 2001

Attest:

NICHOLAS P. GODICI

*Attesting Officer*     *Acting Director of the United States Patent and Trademark Office*